United States Patent [19]

Omura et al.

[11] Patent Number: 4,613,355
[45] Date of Patent: Sep. 23, 1986

[54] ANTIBIOTIC HAVING HERBICIDAL ACTIVITY

[75] Inventors: Satoshi Ōmura, 5-12-7, Seta, Setagaya-ku, Tokyo-to; Haruo Tanaka, Tokyo; Kiyoizumi Hinotozawa, Tokyo; Masatsune Murata, Tokyo; Yuzuru Iwai, Chiba, all of Japan

[73] Assignee: Satoshi Omura, Tokyo, Japan

[21] Appl. No.: 636,643

[22] Filed: Aug. 1, 1984

[30] Foreign Application Priority Data

Aug. 2, 1983 [JP] Japan .................. 58-141401
Feb. 15, 1984 [JP] Japan .................. 59-141401
Mar. 2, 1984 [JP] Japan .................. 59-41065

[51] Int. Cl.$^4$ .................. A01N 57/00; C07K 5/08
[52] U.S. Cl. .................. 71/86; 530/331
[58] Field of Search .................. 71/86; 260/112.5 R

[56] References Cited

U.S. PATENT DOCUMENTS 4,309,208  1/1982  Takematsu et al. .................. 71/86

OTHER PUBLICATIONS

Chem. Abstr. vol. 101; 166778p (1984).
Chem. Abstr. vol. 101, (1984) 206250u.
Chem. Abstr. vol. 102, (1985) 200810a.

*Primary Examiner*—Delbert R. Phillips
*Attorney, Agent, or Firm*—Wolder, Gross & Yavner

[57] ABSTRACT

A compound of the formula $$\begin{array}{c}CH_3\\ \diagdown\\ \phantom{CH_3}\end{array}\!\!\!\overset{O}{\underset{\|}{P}}\!\!-CH_2-CH_2-\underset{\underset{NH_2}{|}}{CH}-CO-NH-\underset{\underset{CH_3}{|}}{CH}-CO-NH-$$
$$\phantom{xxxxxxxxxxxxxxxxxxxxxxxxxxxxxxxxxxxxx}-\underset{\underset{\underset{\underset{CH_3\diagup\phantom{x}\diagdown CH_3}{}}{CH_2}}{CH_2}}{CH}-COOH$$

and salts thereof, exhibits herbicidal activity against many herbaceous and woody plants. The compound may be formulated for agricultural use in conventional manner.

The compound may be made by fermentation of a suitable strain of a microorganism of the genus Kitasatosporia, especially the novel strain Actinomycetes KA-338 (FERM BP-358).

9 Claims, 2 Drawing Figures

Fig. 1

Fig. 2

ANTIBIOTIC HAVING HERBICIDAL ACTIVITY

BACKGROUND OF THE INVENTION

The present invention relates to a new antibiotic, a process for producing it and its use as a herbicide.

Many herbicidal compositions are known which comprise various synthetic substances as active components. However, in view of the increased concern about pollution throughout the world, it is increasingly desirable to provide herbicides which are safely and completely biodegradable. In this regard, it has recently been proposed to use various antibiotics produced by microorganisms as active ingredients of herbicidal compositions. For example, U.S. Pat. No. 3,977,860 discloses the use of N-phosphinomethyl glycine as a herbicide. U.S. Pat. No. 3,832,394 discloses that SF-1293, which is a peptide-type antibiotic having the following structural formula:

is active against certain fungi, and U.S. Pat. No. 4,309,208 discloses the herbicidal use of SF-1293 and shows that this substance exhibits a broader herbicidal spectrum and lower toxicity in comparison with N-phosphinomethyl glycine (glyphosate). To our knowledge, SF-1293 appears to be the only naturally occuring substance having a C-P-C bonding, and its herbicidal activity is likely to be due to the inhibition of glutamine synthetase. JP-A-92628/79 (Kokai Koho 92628/79) discloses a herbicidal composition, comprising as active ingredient, L-2-amino-4-methyl-phosphinobutyric acid, which is obtained by decomposition of SF-1293.

SUMMARY OF THE INVENTION

The present invention is based upon the discovery that a new antibiotic which we have prepared by culturing a microorganism of the Kitasatosporia genus, preferably the strain herein designated Actinomycetes KA-338 (FERM BP-358) has an excellent herbicidal activity and low animal toxicity.

The novel antibiotic, whose properties and structure are more fully described below, is referred to herein for convenience by Phosalacine and may be systematically named phosphinothricyl-alanyl leucine.

The characteristics of Phosalacine of this invention are as follows.

(I) Physico-chemical characteristics:

(1) Elemental analysis: The substance contains carbon, hydrogen, nitrogen, oxygen and phosphorus and does not contain sulfur or halogen. Its elemental analysis is believed to be C: 46.01, H: 7.73, N: 11.50, O: 26.28 and P: 8.48%.

(2) Melting point: Not higher than 225° C. (decomp.).

(3) Molecular weight: 365. An ion peak is noted at 336 (m/z, M$^+$ +1). by FD-mass spectrometry.

(4) Specific rotation: $[\alpha]^{25}_D = -38.8°$ (c=0.65, H$_2$O).

Figure 1:
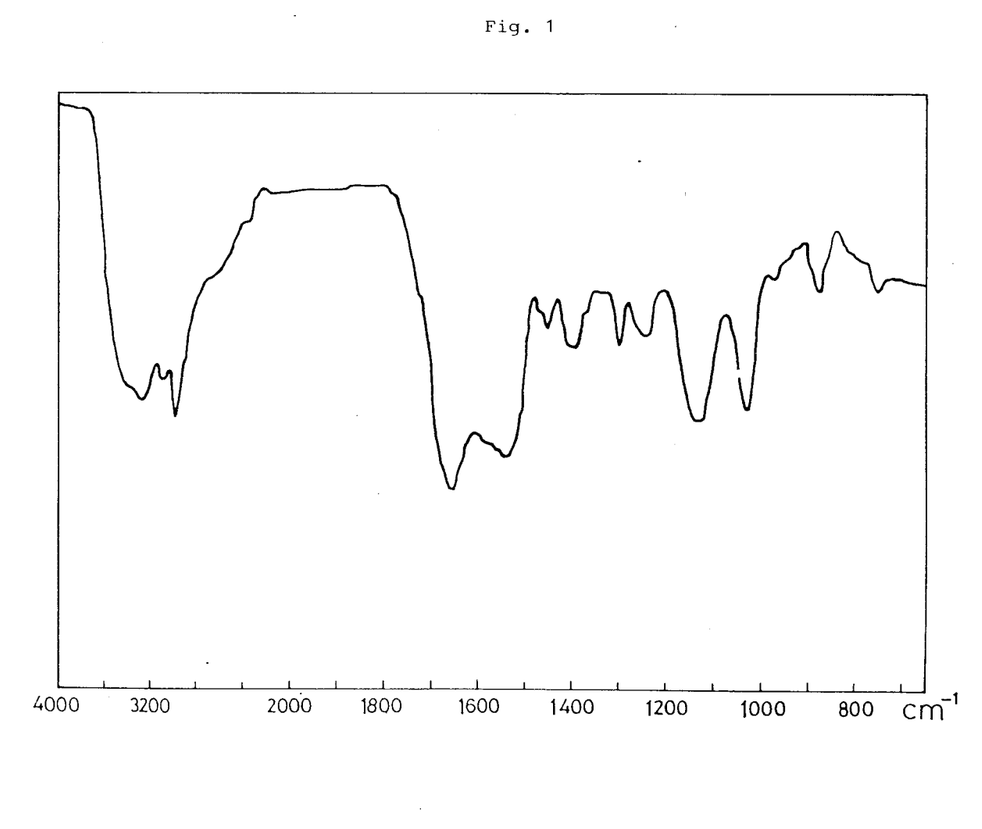

(5) Infrared absorption spectrum: As shown in FIG. 1 of the accompanying drawings (by KBr disc method).

Figure 2:
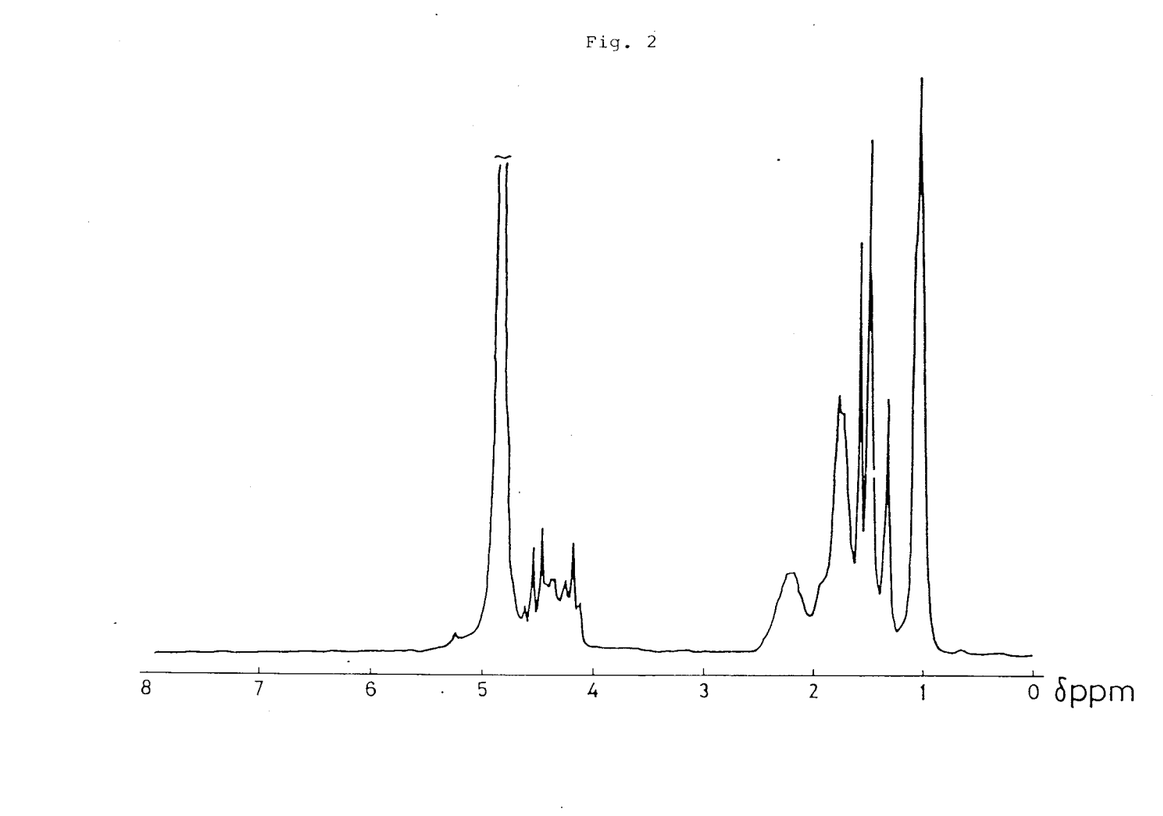

(6) Proton NMR spectrum: As shown in FIG. 2 of the accompanying drawings (in D$_2$O).

(7) Solubility in various solvents: Readily soluble in water, substantially soluble in methanol and sparingly soluble in various organic solvents such as, for example, ethanol, butanol, acetone, ethyl acetate, chloroform, hexane and diethyl ether.

(8) Amphoteric (9) RF values: The RF values indicated in the following table were obtained by thin layer chromatography on silica gel and cellulose carried out by using TLC on aluminium plates having a thickness of 0.2 mm, coated respectively with Kieselgel 60 F254 and Cellulose F254 (commercial products of Merck AG., West Germany) in conventional manner.

TABLE 1

| Solvent system | (Rf values) A | B |
|---|---|---|
| I. Butanol/acetic acid/water (4:1:1) | 0.22 | 0.72 |
| II. Propanol/water (7:3) | 0.38 | 0.75 |
| III. Butanol/methanol/water (4:1:1) | 0.28 | 0.55 |
| IV. Methanol/3% ammonium chloride (7:3) | 0.63 | 0.83 |

[Notes: A ... silica gel, B ... cellulose, Colour was developed by ninhydrin reagent.]

(10) Colour reaction: Positive to ninhydrin reagent.

When Phosalacine is hydrolyzed at a temperature of 110° C. for 18 hours with 6N hydrochloric acid and the resultant solution is subjected to thin layer chromatography on silica gel, there are observed 3 spots, of which 2 spots correspond respectively to the Rf values of leucine and alanine. Moreover, amide I and amide II bands are noted respectively at 1658 and 1545 cm$^{-1}$ in the infrared absorption spectrum as shown in FIG. 1. Furthermore, amino acid analysis, proton NMR spectra and $^{13}$C NMR spectra of various hydrolyzed products of Phosalacine as well as EI-mass spectra of its various derivatives were investigated. As a result, it has been found that the molecular formula of Phosalacine is C$_{14}$H$_{28}$N$_3$O$_6$P and that Phosalacine is a peptide antibiotic, having the following structural formula:

(II) Biological characteristics:

The minimum inhibitory concentrations (MIC values) of Phosalacine were investigated in conventional manner by the agar dilution method and the results are indicated in the following Table, from which it is apparent that Phosalacine is active against various Gram-positive and Gram-negative bacteria and fungi. We noted that the antibacterial activity of Phosalacine was not observed on synthetic media but only on organic media and that, for example, its activity against Bacillus subtilis was competitively antagonised by glutamine in synthetic media.

TABLE 2

| Test microorganism | MIC (ug/ml) | medium |
|---|---|---|
| Staphylococcus aureus KB210 | 0.4 | A |
| Staphylococcus aureus KB199 | 0.2 | A |
| Bacillus subtilis KB211 | 0.4 | A |
| Bacillus cereus KB143 | 0.4 | A |
| Micrococcus luteus KB212 | 6.25 | A |

TABLE 2-continued

| Test microorganism | MIC (ug/ml) | medium |
|---|---|---|
| Escherichia coli KB213 | 12.5 | A |
| Escherichia coli KB176 | 25 | A |
| Klebsiella pneumoniae KB214 | 25 | A |
| Erwinia aroideae KB148 | <0.05 | A |
| Proteus vulgaris KB127 | 25 | A |
| Candida albicans KF1 | >100 | B |
| Aspergillus niger KF105 | >100 | B |
| Mucor racemosus KF223 | 6.25 | B |
| Piricularia oryzae KF180 | 0.1 | B |

[Notes: A ... Davis's minimal medium (pH 7.0), B ... Dextrose Czapek's medium]

Herbicidal activity: As described in detail hereinafter, Phosalacine exhibits herbicidal activity against a wide variety of plants. Its herbicidal spectrum is more or less analogous to that of SF-1293 in view of the fact that Phosalacine also has a C-P-C bonding in its structure. However, its toxicity to animals is significantly and advantageously lower than that of SF-1293.

In summary, Phosalacine is a new compound falling into the class of peptide antibiotics. To our knowledge, SF-1293 and Phosalacine are the only two naturally occurring substances containing a C-P-C bonding. It is possible to use Phosalacine as a herbicide against a wide variety of plants.

According to another aspect of the present invention, there is provided a process for producing Phosalacine, which comprises culturing a microorganism of the genus Kitasatosporia capable of producing Phosalacine in a culture medium to accumulate Phosalacine therein and recovering Phosalacine therefrom.

For the purpose of the present invention, it is possible to use any strain of the genus Kitasatosporia or mutant thereof which is capable of producing Phosalacine by fermentation. Our currently preferred strain is designated Actinomycetes KA-338. We isolated this strain from the soil in Tokyo, Japan and a pure culture thereof has been deposited with Bikoken (the Fermentation Research Institute of Industrial Science and Technology) on 18 July 1983 as FERM BP-358 on the basis of the Budapest Treaty.

The mycological characteristics of Actinomycetes KA-338 (FERM BP-358) are as follows:

(I) Morphological characteristics:

Vegetative hyphae grow well on various agar media and usually no septum is observed. Aerial mycelia grow abundantly on yeast-, malt- and oatmeal agar media and present a velvety appearance. By microscopic observation, sporangiophores in the form of a straight chain (Rectus-Flexibilis type) are prevalent, and 10 or more spores form a chain. The spores measure 0.9×0.9–1.8 μm and are cylindrical. Sclerotium, sporangium and zoospores are not observed.

(II) Cultural characteristics on various media:

The following Table indicates the cultural characteristics of KA-338 on various media, which were investigated with reference to the method by E. B. Shirling and D. Gottlieb [International J. of Systematic Bacteriology, Vol. 16, page 313 (1966)]. In the following Table, the colour and tone of each culture are expressed with reference to Color Harmony Manual, 4th edition, published by Container Corpn. of America, Chicago, U.S.A. (1958) and the code is indicated in the bracket after the colour name. The results indicated herein were noted 2 weeks after the beginning culturing effected at 27° C. unless otherwise specified.

TABLE 3

Cultural characteristics on various media

| Medium | |
|---|---|
| Yeast malt agar | G: Raised and full. Mustard tan (2 lg) |
| | R: Light brown (3 lg) |
| | A: Abundant and velvety. Grey (f) and white (a) |
| | P: Not formed |
| Oatmeal agar | G: Raised and full. Bamboo (2 gc) |
| | R: Bamboo (2 gc) and oatmeal sand (2 ec) |
| | A: Abundant and velvety. Grey (f) and white (a) |
| | P: Not formed |
| Starch-inorganic | G: Diffusible and full. Bamboo (2 gc) |
| | R: Camel (3 ie) and bamboo camel (2 gc) |
| | A: Abundant. Light grey (c) and white (a) |
| | P: Not formed |
| Glycerol-asparagine agar | G: Diffusible and poor |
| | R: White (a) |
| | A: Poor. White (a) |
| | P: Not formed |
| Glucose-asparagine agar | G: Moderate. Bamboo (2 gc) |
| | R: Light mustard tan (2 ie) |
| | A: Moderate. Light grey (c) and white (a) |
| | P: Not formed |
| Peptone-yeast-iron agar | G: Poor |
| | R: Light wheat (2 ea) |
| | A: Not formed |
| | P: Not formed |
| Tyrosine agar | G: Poor |
| | R: White (a) and light grey (c) |
| | A: Poor |
| | P: Not formed |
| Sucrose-nitrate agar | G: Full. Pearl pink (3 ca) |
| | R: Light ivory (2 ca) |
| | A: Moderate. White (a) and light grey (c) |
| | P: Not formed |
| Glucose-nitrate | G: Raised and full. Bamboo (2 gc) |
| | R: Bamboo (2 gc) |
| | A: Moderate. White (a) |
| | P: Not formed |
| Glycerol-calcium malate agar | G: Poor |
| | R: White (a) and grey (b) |
| | A: Poor. White (a) and grey (b) |
| | P: Not formed |
| Glucose peptone agar | G: Moderate. Bamboo (2 gc) |
| | R: Bamboo (2 gc) |
| | A: Poor. White (a) |
| | P: Not formed. |
| Nutrient agar | G: Poor. Light ivory (2 ca) |
| | R: Light ivory (1 ca) |
| | A: Poor. White (a) |
| | P: Not formed |

[Notes: G ... Growth, R ... Reverse, A ... Aerial mycelia, P ... Soluble pigment]

(III) Physiological characteristics:

| | |
|---|---|
| (1) Formation of melanoid pigment | negative |
| (a) Tyrosine agar | negative |
| (b) Peptone-yeast agar | negative |
| (c) Tryptone-yeast liquor | negative |
| (2) Tyrosinase reaction | negative |
| (3) Formation of hydrogen sulfide | negative |
| (4) Reduction of nitrate | positive |
| (5) Liquefication of gelatin | negative |
| (6) Hydrolysis of starch | positive |
| (7) Coagulation of skim milk (37° C.) | negative |
| (8) Peptonization of skim milk (37° C.) | positive |
| (9) Growth temperature and pH ranges | 15–42° C., (5.5–9) |
| (10) Assimilability of carbon sources (Bridham-Gottlieb medium): Assimilable: D-glucose, L-arabinose, D-xylose, L-rhamnose, raffinose, sucrose and D-fructose Not assimilable: i-inositol and D-mannitol | |

| (11) Decomposition of cellulose: | negative |
|---|---|

(IV) Chemical analysis of the cell:

Both LL-type and meso-type diaminopimelic acids are present in the cell wall. The result from the glycolate test was acetyl type. Phospholipid is PII type.

The mycological characterics of KA-338 may be summarized as follows.

With regard to the morphological characteristics, the spore is cylindrical and its surface is smooth. Sclerotum, sporangium and zoospores are not found. With regard to the cultural characteristics, the vegetative hyphae and aerial mycelia are respectively coloured yellow and white. No melanoid pigment or soluble pigment is formed. Moreover, the chemical analysis of the cell wall shows the existence of both LL-type and meso-type diaminopimelic acids in the cell wall. In view of the above-mentioned characteristics, it appears that the present strain is an Actinomycetes strain analgous to *Kitasatosporia setalba* [J. of Antibiotics, Vol. 35, page 1013 (1982)] but the present strain is different from *Kitasatosporia setalba* with regard to the assimilability of D-fructose, sucrose, L-rhamnose and raffinose, the production of soluble pigment (negative), the coagulation of skim milk (negative) and the reduction of nitrate (positive). Thus, it is apparent that the present KA-338 strain is the second microorganism of the genus Kitasatospora to be characterised.

KA-338 may be cultured in conventional manner, for example, by using a liquid medium, and especially good results may be obtained by steep culturing with aeration and agitation. Thus, culture may be effected usually, for example, under aerobic conditions at a temperature of from 20°–40° C. and a pH of 6–7 for a suitable time until a large amount of Phosalacine is accumulated in the cultured broth.

The culturing time may vary with differing conditions and usually the amount of Phosalacine in the cultured broth reaches its maximum, after culturing for e.g. 2–5 days.

The culture media which may be used for the purpose of the present invention may contain suitable amounts of assimilable sources of carbon, nitrogen and inorganic substances which are conventionally used for culturing Actinomycetes. Examples of preferred carbon sources include glucose, maltose, lactose, sucrose, starch, dextrin, oatmeal, glycerol, millet jelly, molasses and the like. Examples of preferred nitorgen sources include soybean meal, corn steep liquor, cotton seed powder, peptone, meat extract, dried yeast, casein hydrolyzate, tomato puree, ammonium salts, nitrates and the like. Preferred examples of inorganic substances are exemplified by sodium chloride, potassium chloride, phosphates and the like. It is possible, if desired, to use suitable organic and inorganic substances for promoting the growth of the strain employed to increase the production yield.

After completion of the fermentation, the cultured broth may be treated in conventional manner, for example, by the individual or combined use of the known methods suitable for isolation and purification of antibiotics having similar physicochemical characteristics to those of Phosalacine as hereinbefore described. Because Phosalacine is present mainly in the liquid phase of the cultured broth and is a water-soluble amphoteric substance, it is advantageous to isolate and purify Phosalacine using, for example, a suitable anion exchange resin, e.g. Amberlite IR120 (commercial product of Rohm and Haas Co., U.S.A.), Dowex 50W (commercial product of Dow Chemical Co., U.S.A.) and the like or a suitable cation exchange resin such as, for example, Amberlite IRA400, IR45 and the like so as to absorb the active substance onto the resin, followed by elution with a suitable acid, alkali or salt solution. Alternatively, the cultured broth may be treated with active carbon, followed by elution of the desired substance with a suitable aqueous organic solvent such as, for example, aqueous acetone, or aqueous methanol. A preferred method of isolation and purification of Phosalacine is exemplified as follows:

The cultured broth is filtered and the filtrate is passed through a column packed with active carbon to adsorb the active material onto the active carbon, which is then eluted with aqueous acetone. The resultant solution containing crude Phosalacine may be purified in conventional manner, for example, by chromatographic treatment on cellulose, silica gel, alumina, Sephadex (commercial product of Pharmacia Fine Chemicals AB., Sweden), Toyopearl (commercial product of Toyo Soda Kogyo K. K., Japan) or the like to obtain purified Phosalacine in the form of an amorphous white powder. It is possible to identify Phosalacine, for example, by the use of a synthetic medium such as Davis's minimal medium, a test microorganism such as Z*Bacillus subtilis*, the paper disc method know per se, or the like.

Phosalacine forms salts with bases, e.g. alkali metal salts and amine salts. Such salts may be made in conventional manner and form a further aspect of our invention. Thus, Phosalacine and its salts may be defined by the following general formula (II):

wherein $M^1$ and $M^2$ are each independently hydrogen or a cation selected, for example, from sodium, potassium, lithium, copper, magnesium, calcium, zinc, nickel, manganese and ammonium which is unsubstituted or substituted by 1–4 lower alkyl, hydroxy lower alkyl or lower alkenyl groups; A is an inorganic or organic acid selected for example, from hydrochloric, sulfuric, hydrobromic, phosphoric, perchloric, nitric, acetic, propionic, citric, tartaric, monochloroacetic, trichloroacetic and trifluoroacetic acids; n is 0, 0.5 or 1; p is the inverse of the valency of $M^1$; and q is the inverse of the valency of $M^2$.

According to a further aspect of our invention, there is provided a herbicidal composition, which comprises an effective amount of at least one compound of the general formula (II) [wherein $M^1$, $M^2$, A, n and q are as hereinbefore defined] as active ingredient, in association with an agriculturally acceptable carrier or excipient.

The term "herbicidal composition" used herein denotes materials which (1) effectively control all plants in a given locus; or (2) selectively control the growth of at least one plant species in the presence of other plants. The term "control" used herein denotes (1) killng, and/or (2) inhibiting the growth, reproduction and/or proliferation, and/or (3) removing, destroying or otherwise diminishing the activity of plants. The term "plant" used herein denotes (1) terrestrial plants inclusive of germinating seeds, emerging seedlings and herbaceous vegetation inclusive of the root and the aerial portion as well as established woody plants and higher fungi; and (2) aquatic plants inclusive algae and other plants which are botanically higher than algae and thus inclusive of vegetative organisms having a floating or submerged habit in water.

It has been found that the herbicidal spectrum of the present herbicidal compounds is at least equal to or superior to that of the known SF-1293. Moreover, the activity of Phosalacine in terms of the effective amount to be applied per unit area, is at least equal to that of SF-1293 and L-2-amino-4-methylphosphino butyric acid. Also, it has been found that the acute animal toxicity of Phosalacine is significantly lower than that of SF-1293 and L-2-amino-4-methyl phosphino butyric acid.

For the preparation of the herbicidal composition of the present invention, it is possible to dissolve Phosalacine in a suitable aqueous solvent without any problem, because Phosalacine is stable at ambient temperature and readily soluble in water. Phosalacine may be used either in the form of the free acid or in the form of suitable salts such as, for example, alkali metal salts or amine salts.

The composition of the present invention may be in the form of a liquid composition prepared by dissolving Phosalacine and/or its salts in a suitable solvent such as water, methanol or a mixture thereof; the composition may, if desired, contain a suitable surfactant. The herbicidal composition may be formulated with a suitable inert carrier or excipient such as, for example, calcium carbonate, kaolin, clay or kieselguhr. Thus, the composition may e.g. be in the form of an aqueous solution, wettable powder, dust or suspension, and may include suitable adjuvants conventionally used in agricultural compositions such as, for example, anti-caking agents, stabilizers, or preservatives.

The herbicidal composition of the present invention may be brought into contact with unwanted plants i.e. plants to be controlled, in conventional manner, for example, by the so-called pre-emergence or post-emergence methods. Thus, the composition may be applied, for example, to the soil surface of orchards, forest lands and the like in order to effectively control unwanted plants including herbaceous and woody plants such as perennial weeds and brush. It is also possible to control unwanted aquatic plants by applying the present composition, for example, to the surface of water where the unwanted plants are located or to the surface of such plants.

The proportion of active ingredient contained in the herbicidal composition may vary, depending upon the active ingredient, the carrier, the types of the plants to be treated, etc. However, in general, the active ingredient may comprise, for example, from 0.01 to 5% by weight of the composition. For example, when a liquid composition is sprayed on herbaceous plants, the proportion of the active ingredient may be from 0.05 to 5% by weight. Concentrated compositions may be diluted prior to use, in conventional manner.

The effective application rates for Phosalacine will depend on various factors such as, for example, the types and leaf ages of the plants, the method and purpose of the application, etc; but for general guidance we suggest rates in the range 0.1 to 10 kg/ha, calculated as Phosalacine free acid, for use on terrestrial plants. For instance, for use on weeds not exceeding 10 cm in height one may spray, at a rate of 1000-5000 l/ha, an aqueous solution of Phosalacine at a concentration of e.g. 50-500 ppm. For weeds of 10-30 cm in height we prefer a solution containing 250-2000 ppm of Phosalacine. It is also possible to apply Phosalacine to aquatic plants, for example, at a rate of from 0.01 to 1000 ppm (calculated as free acid) in the aquatic environment.

The acute toxicity of Phosalacine to fish is lower than the corresponding values of SF-1293 (whose $LD_{50}$ is more than 20 ppm according to JP-A-9003/80) and of L-2-amino-4-methylphosphino butyric acid.

The herbicidal effect of Phosalacine may further be improved by using its salts which may be prepared in conventional manner. Preferred salts of Phosalacine include, for example, metallic salts, in particular alkali metal salts such as mono- and disodium salts and mono- and dipotassium salts; and mono- and diamine salts such as, for example, salts with ethanolamine, ethylamine, n-butylamine or isopropylamine (cf. the general formula II as defined above).

The following Table indicates by way of illustration only examples of preferred plants which may be controlled by the present herbicidal composition.

TABLE 4

| Plant No. | Common name used in Japan (Botanical name) |
| --- | --- |
| 1. | Yomogi (*Artemisia princeps*) |
| 2. | Gishigishi (*Rumex japonicus*) |
| 3. | Hamasuge (*Cyperus rotundus*) |
| 4. | Miyako-zasa (*Sasa nipponica*) |
| 5. | Susuki (*Miscanthus sinensis*) |
| 6. | Yama-tsutsuji (*Rhododendron haempferi*) |
| 7. | Kuma-ichigo (*Rubus crataegifolius*) |
| 8. | Kuri (*Castanea crenata*) |
| 9. | Konara (*Quercus serrata*) |
| 10. | Mehishiba (*Digitaria adscendens*) |
| 11. | Azuma-nezasa (*Pleioblastus chino*) |
| 12. | Kikuimo (*Helianthus tuberosus*) |
| 13. | Yabukarashi (*Cayratia japonica*) |
| 14. | Ezono gishigishi (*Rumex obtusifolius*) |
| 15. | Chigaya (*Imperata cyrindrica*) |
| 16. | Kuzu (*Pueraria lobata*) |
| 17. | Sarutori-bara(*Smilax china*) |
| 18. | Kiichigo (*Rubus palmatus*) |
| 19. | Sanshou (*Zanthoxylum piperitum*) |
| 20. | Warabi (*Pteridium aquilinum*) |
| 21. | Gamazumi (*Viburnum dilatatum*) |
| 22. | Akamatsu (*Picea densiflora*) |
| 23. | Karamatsu (*Larix leptolepis*) |
| 24. | Shikoku-bie (*Eleucine indica* var. *carocana*) |
| 25. | Rikutou (*Oryzae sativa*) |
| 26. | Komugi (*Triticum aestivum*) |
| 27. | Negi (*Allium fistulosum*) |
| 28. | Kanran (*Brassica oleracea*) |
| 29. | Ninjin (*Daucus carota*) |
| 30. | Gobou (*Arctium lappa*) |
| 31. | Nasu (*Solanum melongena*) |
| 32. | Daikon (*Raphanus sativus*) |
| 33. | Kiuri (*Cucumis sativus*) |
| 34. | Daizu (*Glycine max*) |
| 35. | Katabami (*Oxalis corniculata*) |
| 36. | Konishikisou (*Euphonia supina*) |

TABLE 4-continued

| Plant No. | Common name used in Japan (Botanical name) |
|---|---|
| 37. | Hotei-aoi (*Eichhornia crassipes*) |
| 38. | Ukikusa (*Spirodela polyrhiza*) |
| 39. | Omodaka (*Sagittaria trifolia*) |
| 40. | Ao-ukikusa (*Nenna pauciocostata*) |
| 41. | Urikawa (*Sagittaria pygmaea*) |
| 42. | Tochikagami (*Hydrocharia dubia*) |
| 43. | Aginashi (*Sagittaria aginashi*) |
| 44. | Ao-midoro (*Spirogira crassa*) |
| 45. | Ami-midoro (*Hydrodictyon reticulatum*) |
| 46. | Keiso rui (*Bacillariophyta*) |
| 47. | Matsumo (*Ceratophyllum demersum*) |
| 48. | Shakujimo (*Chara braunii*) |
| 49. | Sanshoumo (*Salvina natans*) |

The following non-limiting Examples illustrate the present invention.

EXAMPLE 1

A seed medium (100 ml) containing glucose (0.1%), starch (2.4%), peptone (0.3%), meat extract (0.3%), yeast extract (0.5%) and calcium carbonate (0.4%) and a main medium (20 l) containing glucose (0.2%), tomato puree (4.0%) and oatmeal (1.5%) were adjusted to a pH of 7.0 and sterilized at 121° C. for 15 minutes. A platinum loop of Actinomycetes KA-338 (FERM BP-358) was taken from a slant culture and transferred to the seed medium for culturing at 27° for 2 days with shaking. The resultant seed was transferred to the main medium in a 30 l jar fermentor at a ratio of 1%, and cultured at 27° C. for 68 hours with aeration (10 l/min) and rotation (250 r.p.m.). After completion of fermentation, the cultered broth (20 l) was centrifuged by using a sharpless-type centrifuge to separate the cells from the filtrate. The filtrate was adjusted to a pH of 2.0 with 6N-hydrochloric acid and was passed through a column packed with active carbon (800 g) to adsorb the active material onto the active carbon which was washed with water (20 l), followed by elution with 30% aqueous acetone. The effluent was divided into fractions (each one liter). The active fractions Nos. 1 to 8 in Erlenmeyer flasks were concentrated under reduced pressure, collected, combined and freeze-dried to obtain crude powders coloured light yellowish brown (12 g).

The powders were transferred to a column packed with cellulose (380 g) and filled with a mixture of ethanol/water (20:1). The elution was effected with a solvent system of ethanol/water (10:1), and the effluent was divided into fractions (each 18 ml). The active fraction Nos. 60–110 were collected, combined, concentrated under reduced pressure and freeze-dried to obtain a powder (3.5 g) which was then transferred to a column packed with cellulose (210 g) and filled with a mixture of butanol/acetic acid/water at a ratio of 160:1:2. A solvent system of butanol/acetic acid/water (80:1:2) was used for elution. The effluent was divided into fractions (each 18 ml). The active fraction (Nos. 27 to 55) were collected, combined, concentrated under reduced pressure and freeze-dried to obtain a powder (2.0 g) which was transferred to a column packed with Toyopearl HW-40, (500 ml: commercial product of Toyo Soda Kogyo K. K., Tokyo) filled with distilled water. The elution was effected with distilled water and the effluent was divided into fractions (each 18 ml). The active fractions (Nos. 19–39) were collected, combined and freeze-dried to obtain a powder (1.1 g) which was transferred to a column packed with Sephadex LH-20 (700 ml: commercial product of Pharmacia Fine Chemicals AB., Sweden) filled with distilled water. Elution was effected with distilled water, and the effluent was divided into fractions (each 10 ml). The active fractions (Nos. 55–66) were collected, combined, concentrated and freeze-dried to obtain a light yellowish white powder (600 mg).

For further purification, the powder (370 mg) was fractionated using Avicel SF (commercial product of Funakoshi, Japan) and a solvent system of propanol/acetic acid/water (4:1:1) with reference to an Rf value of 0.72 to obtain a white powder (210 mg). The resultant powder was then transferred to a column packed with Toyopearl HW-40 (500 ml) and filled with water. The development was effected with distilled water and the effluent was divided into fractions (each 5 ml). The active fractions (Nos. 48–68) were collected, combined, concentrated under reduced pressure and then freeze-dried to obtain a white powder (160 mg). This powder was then transferred to a column packed with Sephadex LH-20 (700 ml; filled with distilled water) and developed with distilled water. The effluent was divided into fractions (each 5 ml) which were then subjected to cellulose thin layer chromatography using cellulose F254 (commercial product of Merck Ag., West Germany) and a solvent system of butanol/acetic acid/water (4:1:1) with reference to an Rf value of 0.72. The resultant single spot was noted to identify the active fractions, on each occasion. The active fractions (Nos. 79–89) were collected, combined, concentrated under reduced pressure and then freeze-dried to obtain Phosalacine in the form of a white powder having the physico-chemical characteristics described above (130 mg).

EXAMPLE 2

A liquid medium (1 l) containing glucose (0.1%), starch (2.4%), peptone (0.3%), meat extract (0.3%, yeast extract (0.5%) and $CaCO_3$ (0.4%) [pH7] was used for culturing Actinomycetes KA-338 (FERM BP-358) at 27° C. for 48 hours with aeration and agitation to obtain a seed culture which was further cultured at 27° C. for 72 hours by using a liquid medium (70 l; pH6.0) containing tomato puree (4.0%), glucose (0.2%), oatmeal (1.5%) and $CoCl_2.2H_2O$ (50 mcg/l) with aeration. After completion of the fermentation, the cultured broth was adjusted to a pH of 6.0 and centrifuged by using a sharpless-type centrifuge to obtain a supernatant which was pased through a column (1.4 l) packed with Diaion WA-30 (OH—form) [a weakly basic anion exchange resin commercially available from Mitsubishi Kasei Kogyo K. K., Tokyo] to adsorb the active material onto the resin. After washing with water, the column was eluted with 0.5N hydrochloric acid, and the effluent was divided into fractions (each 500 ml). The active fractions (Nos. 3–10) were collected and combined, and the combined fractions were passed through a column (5×31.5 cm) packed with active carbon to adsorb the active material. After washing with water, the column was eluted with 30% aqueous acetone, and the effluent was divided into fractions (each 20 ml). The active fractions (Nos. 15–55) were collected and combined, and the combined fractions were passed through a column (5×27 cm) packed with a strongly acidic anion exchange resin [Amberlite IR120, commercial product of Rohm and Haas Co., U.S.A.] to adsorb the active material. After washing with water, the column was eluted with 0.5N ammonium hydroxide and the effluent was divided into fractions (each 20 ml). The active fractions (Nos. 98–152) were collected, combined and concentrated under reduced pressure. The concentrated solution was precipitated with ethanol (200 ml). The supernatant was collected and concentrated under reduced pressure, followed by addition of acetone (×20) to obtain 1.44 g of Phosalacine. The resultant product was then dissolved in water, neutralized with 1N NaOH and concentrated and dried to obtain Phosalacine sodium salt (1.5 g). 1N NaOH (1 mmol; 1 ml) was added to a small amount of water containing Phosalacine (free acid; 365 mg; 1 mmol) and the mixture was concentrated to obtain Phosalacine sodium salt (379 mg). Similarly, 1N NaOH (2 ml) was added to a solution containing Phosalacine (365 mg) to obtain the disodium salt of Phosalacine (411 mg). By using 1N KOH instead of 1N NaOH, mono- and dipotassium salts of Phosalacine were obtained (respectively 404 mg and 433 mg).

EXAMPLE 3

(Aqueous solution)

Phosalacine (free acid; 30.00%), octylphenylpolyoxy ethanol (15.00%) and methyl parahydroxybenzoate (0.15%) were mixed together and dissolved in water (54.85%). The resultant aqueous solution may be diluted with water for use as a herbicide.

EXAMPLE 4

(Wettable powder)

Phosalacine (free acid; 50.0%), kieselguhr (45.0%) and monosorbitan alkylester (5.0% as surfactant) were uniformly mixed together and finely grounded. The resultant wettable powder may easily be dispersed in water for use.

EXAMPLE 5

(Dusting agent)

Phosalacine (free acid; 5%) and talc (95%) were well mixed together and ground to obtain a dusting agent.

Unless otherwise specified, the following materials were used in the Examples described hereinafter:
(a) Phosalacine sodium salt was monosodium salt.
(b) SF-1293 and its monosodium salt were prepared by the method described in U.S. Pat. No. 3,832,394.
(c) As glyphosate, Round Up (commercial product of Monsanto Chemical Co., U.S.A.) was used.
(d) L-2-amino-4-methylphosphino butyric acid was prepared by the method described in JP-A-85538/73.

EXAMPLE 6

(Pre-emergence test)

Upland soil was put in a pot of 10 cm diameter and the seeds of *Digitaria adscendens* were sown in the soil surface at a depth of 1 cm. After compacting the soil surface gently, the soil was sprayed evenly with solutions of Phosalacine sodium salt dissolved at different concentrations in water (each 5 ml). 10 days later, the number of emerged seedlings was counted and the percentage inhibition of emergence was evaluated by comparison with untreated plots. For comparison, a similar test was carried out using glyphosate (monosodium salt) instead of Phosalacine salt. The results shown in the following Table indicate that the pre-emergence effect of Phosalacine was better than that of glyphosate.

TABLE 5

| Compound | Percent inhibition of emergence | | | | |
|---|---|---|---|---|---|
| | 0 | 500 | 1000 | 2500 | g/ha |
| Phosalacine (Na salt) | 0 | 80 | 100 | 100 | |
| Glyphosate (control) | 0 | 0 | 0 | 0 | |

EXAMPLE 7

Upland soil was put in a pot of 10 cm diameter and the seeds of *Digitaria adscendens* were sown in the soil at a depth of 1 cm from the surface. When the height of the seedlings was about 10 cm, aqueous solutions of the test compounds as shown in the following Table were uniformly sprayed on the plants at a rate of 1.2 ml per plant, equivalent to 1000 liter per hectare. 10 days after the foliage treatment, damage to plants was visually assessed on a scale of from 0 to 10, where 0 indicates no effect and 10 indicates complete kill.

| Scale of foliage damage (%) | | | | | | | | | | | |
|---|---|---|---|---|---|---|---|---|---|---|---|
| Scale | 0 | 1 | 2 | 3 | 4 | 5 | 6 | 7 | 8 | 9 | 10 |
| Damage (%) | 0 | 10 | 20 | 30 | 40 | 50 | 60 | 70 | 80 | 90 | 100 |

TABLE 6

| Test compound | Concentration (ppm) | | | |
|---|---|---|---|---|
| | 0 | 0.01 | 0.03 | 0.1 |
| Phosalacine Na salt | 0 | 3 | 10 | 10 |
| monodiethylamine salt | 0 | 5 | 10 | 10 |
| Glyphosate (control) | 0 | 0 | 5 | 10 |

EXAMPLE 8

Aqueous solutions of Phosalacine (Na salt) at different concentrations were applied at a rate of 1500 liters per hectare to naturally occurring plants or plants which were cultured on plates as shown in the following Table at certain stages of growth. The Phosalacine applied contained 0.1% of octylphenylpolyoxy ethanol as surfactant. 7 and 14 days after the foliage treatment, damage to the plants was visually assessed on a scale of from 0 to 5 where 0 indicates no effect and 5 indicates complete kill. The results shown in the followint Table indicate that Phosalacine exhibited a non-selective herbicidal activity against various plants at a lower concentration than SF-1293. One month after the foliage treatment, the inhibition of regrowth of the plants was visually investigated. The ability of Phosalacine to inhibit regrowth was equal or superior to that of SF-1293.

TABLE 7

| Compound No. | 7 days | | | | 14 days | | | |
|---|---|---|---|---|---|---|---|---|
| | P | | SF | | P | | SF | |
| | % 0.05 | 0.1 | 0.1 | 0.2 | 0.05 | 0.1 | 0.1 | 0.2 |
| 1 | 3 | 5 | 3 | 4 | 4 | 5 | 4 | 5 |
| 5 | 3 | 5 | 3 | 4 | 4 | 5 | 4 | 5 |
| 10 | 3 | 5 | 3 | 5 | 4 | 5 | 4 | 5 |
| 11 | 3 | 5 | 3 | 4 | 4 | 5 | 4 | 5 |
| 12 | 3 | 5 | 3 | 4 | 4 | 5 | 4 | 5 |
| 13 | 3 | 5 | 3 | 4 | 4 | 5 | 4 | 5 |
| 14 | 3 | 5 | 3 | 4 | 4 | 5 | 4 | 5 |
| 15 | 3 | 5 | 3 | 4 | 4 | 5 | 4 | 5 |
| 16 | 3 | 5 | 3 | 4 | 4 | 5 | 4 | 5 |
| 24 | 3 | 5 | 3 | 4 | 4 | 5 | 4 | 5 |
| 25 | 3 | 5 | 3 | 4 | 4 | 5 | 4 | 5 |
| 26 | 3 | 5 | 3 | 4 | 4 | 5 | 4 | 5 |
| 27 | 3 | 5 | 3 | 5 | 5 | 5 | 4 | 5 |
| 28 | 3 | 5 | 3 | 4 | 4 | 5 | 4 | 5 |

| Compound | | 7 days | | | | 14 days | | | |
|---|---|---|---|---|---|---|---|---|---|
| | | P | | SF | | P | | SF | |
| No. | % 0.05 | 0.1 | 0.1 | 0.2 | 0.05 | 0.1 | 0.1 | 0.2 |
| 29 | 3 | 5 | 2 | 3 | 4 | 5 | 4 | 5 |
| 30 | 3 | 5 | 3 | 5 | 4 | 5 | 4 | 5 |
| 31 | 3 | 5 | 3 | 5 | 5 | 5 | 4 | 5 |
| 32 | 3 | 5 | 3 | 4 | 4 | 5 | 4 | 5 |
| 33 | 3 | 5 | 3 | 4 | 4 | 5 | 4 | 5 |
| 34 | 3 | 5 | 3 | 4 | 5 | 5 | 4 | 5 |
| 35 | 3 | 5 | 3 | 4 | 4 | 5 | 4 | 5 |
| 36 | 3 | 5 | 3 | 4 | 4 | 5 | 4 | 5 |

P: Phosalacine (mono Na salt).
SF: SF-1293 substance (mono Na salt)
No: Plant Number (cf. Table 1)
*Concentration of the test compound is indicated by %.

This Table indicates that Phosalacine exhibited a non-selective herbicidal activity at a lower concentration than SF-1293. One month after the foliage treatment, the inhibition of regrowth of the plants was visually assessed. The regrowth inhibiting activity of Phosalacine was equal or superior to that of SF-1293.

EXAMPLE 9

Aqueous solutions of Phosalacine (Na salt) at different concentrations and 0.1% of octylphenylpolyoxy ethanol as surfactant were applied to the area where various weeds and brush were naturally growing at a rate of 1500 liter per hectare. One month after the foliage treatment, damage to weeds and brush was visually assessed on a scale of from 0 to 5 where 0 indicates no effect and 5 indicates complete kill as hereinbefore defined.

TABLE 8

| Compound, % conc | | OE | 8* | 17* | 18* | 19* | 20* | 21 |
|---|---|---|---|---|---|---|---|---|
| SF | 0.05% | 2 | 2 | 2 | 2 | 2 | 2 | 2 |
| | 0.1% | 4 | 4 | 4 | 4 | 4 | 4 | 4 |
| | 0.2% | 5 | 5 | 5 | 5 | 5 | 5 | 5 |
| PH | 0.05% | 3 | 3 | 3 | 3 | 3 | 3 | 3 |
| | 0.1% | 5 | 5 | 5 | 5 | 5 | 5 | 5 |
| | 0.2% | 5 | 5 | 5 | 5 | 5 | 5 | 5 |

SF . . . SF-1293 substance (Na salt), PH . . . Phosalacine (Na salt), OE . . . overall evaluation, * . . . Plant Number (cf. Table 1),

EXAMPLE 10

Aqueous solutions containing Phosalacine (Na salt) at different concentrations and 0.1% of octylphenylpolyoxy ethanol as surfactant were applied at a rate of 1500 liter per hectare to woody plants of about 60–70 cm in height. 7 and 14 days after the foliage treatment, damage to the plants was visually assessed on a scale of from 0 to 5 (cf. Example 7). The results are shown in the following Table, from which it is apparent that Phosalacine is not herbicidally active against *Chamaecyparis obtusa* even when applied at a concentration of 0.5% and also exhibits a relatively low herbicidal activity against *Cryptomeria japonica*. Thus, Phosalacine may be used to selectively control weeds and brush in forestry cultivations of such useful plants.

TABLE 9

| Compound (%) | | 7 days | | | | | 14 days | | | | |
|---|---|---|---|---|---|---|---|---|---|---|---|
| | | 22* | 23* | CH | CP | 8* | 22* | 23* | CH | CP | 8* |
| SF | 0.125 | 4 | 4 | 0 | 0 | 5 | 5 | 5 | 0 | 0 | 5 |
| | 0.25 | 4 | 4 | 0 | 0 | 5 | 5 | 5 | 0 | 1 | 5 |
| | 0.5 | 4 | 4 | 0 | 0 | 5 | 5 | 5 | 0 | 2 | 5 |
| PH | 0.125 | 4 | 4 | 0 | 0 | 5 | 5 | 5 | 0 | 0 | 5 |
| | 0.25 | 4 | 4 | 0 | 0 | 5 | 5 | 5 | 0 | 1 | 5 |
| | 0.5 | 4 | 4 | 0 | 0 | 5 | 5 | 5 | 0 | 2 | 5 |

SF. . .SF-1293 substance (Na salt), PH. . .Phosalacine (Na salt), CH:*Chamaecyparis obtusa* CP:*Cryptomeria japonica*. *Plant No. (cf. Table 1)

EXAMPLE 11

Aqueous solutions containing different salts of Phosalacine at different concentrations as active ingredients and 0.1% of octylphenylpolyoxy ethanol as surfactant were applied at a rate of 1000 liter per hectare to *Rumex obtusifolius* (Plant No. 14) at a certain stage of growth. 21 days after foliage treatment, damage to the plant was visually assessed on a scale of 0 to 5 as hereinbefore described. The salts used were prepared by the methods described in the reference mentioned above. The results are shown in the following Table, from which it is apparent that various salts of Phosalacine exhibited herbicidal activities at a concentration of from 0.05 to 0.1%.

TABLE 10

| | Damage to plants after 21 days | |
|---|---|---|
| Phosalacine salt | 0.05% | 0.1% |
| Mono Na salt | 3 | 5 |
| Di Na salt | 3 | 5 |
| Mono Ka salt | 3 | 5 |
| Di Ka salt | 3 | 5 |
| Mono isopropylamine salt | 3 | 5 |
| Mono n-butylamine salt | 3 | 5 |

EXAMPLE 12

(activity against aquatic plants)

An aqueous solution containing 0.1% of Phosalacine (monosodium salt) and 0.1% of octylphenylpolyoxyethanol was applied to *Eichhornia crassipes* at a certain stage of growth, at a rate of 1500 liter per hectare as a foliage treatment. Damage to the plants was assessed visually 4 weeks after the treatment. The treated plants were completely killed, while the untreated plants were normal.

EXAMPLE 13

Killifishes (Japanese name, Medaka), were obtained from a market and maintained in a water bath at 25±2° C. for a week. Then the fishes (each group consisting of 10 fishes) were placed in water baths containing the test compounds at given concentrations as shown in the following Table. 24 and 48 hours after this, the survival ratio (%) of each group was visually counted to assess the acute toxicity.

TABLE 11

| | | Survival ratio (%) after | |
|---|---|---|---|
| Compound (ppm) | | 24 | 48 hours |
| Phosalacine | 20 | 100 | 100 |
| Mono Na salt | 100 | 100 | 50 |
| | 500 | 0 | 0 |

TABLE 11-continued

| Compound (ppm) | | Survival ratio (%) after | |
|---|---|---|---|
| | | 24 | 48 hours |
| Glyphosate | 200 | 0 | 0 |
| L-2-amino-4-methyl phosphino butyric acid | 100 | 0 | 0 |
| Untreated | | 100 | 100 |

From this Table, it is apparent that the acute toxity of Phosalacine against fish is less than that of glyphosate and SF-1293 [LD$_{50}$ of SF-1293 being >20 ppm according to JP-A-9003/80].

EXAMPLE 14

Mice [ICR (RJ) strain; female; 6 weeks after birth; each group consisting of 10 mice] were used as test animals to investigate the acute toxity of Phosalacine in mice. A 1% aqueous solution (free acid) was forcibly administered per os to each animal and the body weight of each animal was measured 7 and 14 days after administration. The results are shown in the following Table. Separately, a similar test was effected by administering Phosalacine (free acid) at a dose of 100 mg/kg. No significant change of body weight was noted. Thus, it has bee found that the acute toxity of Phosalacine to mice is very low.

TABLE 12

| Dose | Body weight (g) | | |
|---|---|---|---|
| | After 0 | 7 | 14 days |
| 500 mg/kg | 23.9 | 24.5 | 26.2 |
| Untreated | 23.5 | 23.7 | 25.9 |

We claim:
1. A compound of the formula and salts thereof.

2. A compound of the formula wherein $M^1$ and $M^2$ are each independently hydrogen or a cation selected from sodium, potassium, lithium, copper, magnesium, calcium, zinc, nickel, manganese and ammonium which is unsubstituted or substituted by 1–4 lower alkyl, lower hydroxyalkyl or lower alkenyl groups; A is an inorganic or organic acid selected from hydrochloric, sulfuric, hydrobromic, phosphoric, perchloric, nitric, acetic, propionic, citric, tartaric, monochloroacetic, trichloroacetic and trifluoroacetic acids; n is 0, 0.5 or 1; p is the inverse of the valency of $M^1$; and q is the inverse of the valency of $M^2$.

3. Mono- and di-sodium salts of the compound of claim 1.

4. Amine salts of the compound of claim 1.

5. A herbicidal composition comprising an effective amount of a herbicidal compound and an agriculturally acceptable carrier and/or adjuvant, characterised in that said herbicidal compound comprises a compound of any of claims 1 to 4.

6. A method for the control of unwanted vegetation by applying to the locus of such vegetation an effective amount of a herbicidal compound, characterised in that said herbicidal compound comprises a compound of any of claims 1 to 4.

7. A method of claim 6 wherein herbaceous plants are controlled.

8. A method of claim 6 wherein brush and woody plants are controlled.

9. A method of claim 6 wherein aquatic plants are controlled.